(12) United States Patent
Igwebuike et al.

(10) Patent No.: US 10,231,876 B2
(45) Date of Patent: Mar. 19, 2019

(54) MEDICAL DRESSING

(71) Applicant: Coloplast A/S, Humlebaek (DK)

(72) Inventors: Henning Igwebuike, Lynge (DK);
Grazyna Hansen, Frederiksberg C
(DK); Jan Marcussen, Taastrup (DK);
Thomas Jon Jensen, Gentofte (DK)

(73) Assignee: Coloplast A/S, Humlebaek (DK)

( * ) Notice: Subject to any disclaimer, the term of this patent is extended or adjusted under 35 U.S.C. 154(b) by 642 days.

(21) Appl. No.: 14/872,253

(22) Filed: Oct. 1, 2015

(65) Prior Publication Data

US 2016/0022505 A1  Jan. 28, 2016

Related U.S. Application Data

(63) Continuation-in-part of application No. PCT/DK2014/050070, filed on Mar. 24, 2014.

(30) Foreign Application Priority Data

Apr. 3, 2013  (DK) ................... 2013 70184

(51) Int. Cl.
*A61F 13/02* (2006.01)
*A61K 9/70* (2006.01)
(Continued)

(52) U.S. Cl.
CPC .... *A61F 13/0223* (2013.01); *A61F 13/00063* (2013.01); *A61F 13/025* (2013.01); *A61F 13/0213* (2013.01); *A61K 9/70* (2013.01); *A61K 9/7023* (2013.01); *A61K 9/7038* (2013.01); *A61F 2013/00285* (2013.01); *A61F 2013/00902* (2013.01); *A61F 2013/00906* (2013.01); *A61L 15/44* (2013.01)

(58) Field of Classification Search
CPC .. A61F 13/00063; A61F 13/02; A61F 13/025; A61F 2013/00285; A61F 2013/00902; A61F 2013/00906; A61F 2013/0091; A61K 9/70; A61K 9/7023; A61K 9/7038; A61L 15/00; A61L 15/44
USPC ....... 128/849; 602/48, 54–56; 424/443, 445, 424/447–449
See application file for complete search history.

(56) References Cited

U.S. PATENT DOCUMENTS 4,231,369 A    11/1980  Soerensen et al.
4,307,717 A *  12/1981  Hymes ............... A61B 5/04087
                                                        106/139.2
(Continued)

FOREIGN PATENT DOCUMENTS

JP    1993192363 A2    8/1993
JP    2001509694 T2    7/2001
(Continued)

*Primary Examiner* — Keri J Nelson
(74) *Attorney, Agent, or Firm* — Coloplast Corp., Coloplast A/S; Nick Baumann

(57) ABSTRACT

A medical dressing comprising an absorbent adhesive layer having a pharmaceutically active agent incorporated, the non-skin-facing surface being provided with a backing layer and the skin facing surface being interrupted by a pattern of cavities. The cavities provide a storage room and distribution centre for wound exudates enabling the dressing to be applied to fast exuding wounds and at the same time allows for an increased initial release of the pharmaceutically active agent.

19 Claims, 2 Drawing Sheets

(51) Int. Cl.
*A61L 15/44* (2006.01)
*A61F 13/00* (2006.01)

(56) References Cited

U.S. PATENT DOCUMENTS

| | | | |
|---|---|---|---|
| 4,367,732 A | 1/1983 | Poulsen et al. | |
| 4,867,748 A | 9/1989 | Samuelsen | |
| 5,133,821 A | 7/1992 | Jensen | |
| 5,308,313 A * | 5/1994 | Karami | A61F 13/025 |
| | | | 602/54 |
| 5,643,187 A | 7/1997 | Naestoft et al. | |
| 5,714,225 A | 2/1998 | Hansen et al. | |
| 6,726,791 B1 | 4/2004 | Oeelund et al. | |
| 6,893,655 B2 * | 5/2005 | Flanigan | A61K 9/703 |
| | | | 424/443 |
| 8,329,976 B2 * | 12/2012 | Freiding | A61F 13/0276 |
| | | | 602/41 |
| 8,410,332 B2 * | 4/2013 | Burton | A61F 13/0203 |
| | | | 602/41 |
| 2004/0208914 A1 * | 10/2004 | Richlin | A61K 9/0014 |
| | | | 424/448 |
| 2006/0211972 A1 * | 9/2006 | Nielsen | A61L 15/28 |
| | | | 602/48 |
| 2009/0216168 A1 | 8/2009 | Eckstein | |

FOREIGN PATENT DOCUMENTS

| | | |
|---|---|---|
| JP | 2002525219 T2 | 8/2002 |
| JP | 2003522596 T2 | 7/2003 |
| JP | 2009534057 T2 | 9/2009 |
| JP | 2014511851 T2 | 5/2014 |
| WO | 1998017328 A1 | 4/1998 |
| WO | 2000018554 A1 | 4/2000 |
| WO | 0160296 A1 | 8/2001 |
| WO | 2001060296 A1 | 8/2001 |
| WO | 2007121744 A1 | 11/2007 |
| WO | 2010135645 A2 | 11/2010 |
| WO | 2012136218 A1 | 10/2012 |
| WO | 2013044924 A1 | 4/2013 |

* cited by examiner

MEDICAL DRESSING

FIELD OF THE INVENTION

The present invention relates to a medical dressing for application to the skin, e.g. a blister, or a wound, wherein the dressing comprises a pharmaceutically active agent incorporated in an absorbent adhesive layer. The dressing has a skin-facing surface interrupted by a pattern of cavities allowing for an increased initial release of a pharmaceutically active agent.

BACKGROUND

Wound dressings comprising a backing layer and a layer of hydrocolloid adhesive are well known, such dressings may be known as hydrocolloid dressings. Whereas these dressings are excellent for application to blisters or slowly exuding wounds, they may be difficult to attach to fast exuding wounds, such as a bleeding wound or skin abrasion. Hydrocolloid adhesive is capable of absorbing large amounts of moisture, but not instantaneously as their initial absorption is low.

Typically, the hydrocolloid dressings have a continuous surface against the skin or wound which does not absorb liquid instantaneously. This leads to the issue of small drops of fluid being squeezed across the surface of the dressing during application of the dressing to the wound and this fluid may be squeezed all the way to the edge of the dressing leading to poor adhesion and premature detachment. There have been different attempts to solve problems with initial absorption:

One approach is to optimize the adhesive to a faster initial absorption, e.g. by increasing the amount of hydrocolloid. However, the increase in hydrocolloid may lead to a decrease in adhesive tack and thereby a shorter wear time for the wound dressing. Thus, the increase in absorption rate required to deal with the fluid production rate is not compatible with a well adhering hydrocolloid dressing.

Another way is to provide the wound dressing with an absorbent center zone, such as a pad of an absorbent material, such as a gauze or foam or cellulosic material. This will add an extra step in the production and the resulting product may be more visible and less flexible. Furthermore, adding an absorbent pad fundamentally changes the nature of the hydrocolloid dressing as the benefits of having the hydrocolloid adhesive over the wound bed will not be present anymore.

An object of the present invention is to provide an absorbent dressing capable of providing an increased initial release of a pharmaceutically active agent directly to e.g. a blister or open wound. It is an additional object of the present invention to provide such an absorbent dressing that can handle exudates from wounds and e.g. rupturing blisters while providing said initial release directly thereto.

SUMMARY OF THE INVENTION

The present invention relates in a first aspect to a medical dressing comprising an absorbent adhesive layer having a skin-facing surface and a non-skin-facing surface, the non-skin-facing surface being provided with a backing layer, the skin-facing surface being interrupted by a pattern of cavities, and wherein the absorbent adhesive layer comprises a pharmaceutically active agent. The medical dressing may for example be used to handle exudates while releasing an active agent to wounds, skin abrasions or blisters. For cases where such wounds, skin abrasions or blisters are causing a subject pain, the active agent may for instance be analgesic agents, anti-inflammatory agents or local anesthetic agents.

In a second aspect, the invention relates to a method of treating pain in a wound, a skin abrasion or on a blister, the method comprises the step of applying to said wound, skin abrasion or blister a medical dressing comprising an absorbent adhesive layer having a skin-facing surface and a non-skin-facing surface, the non-skin-facing surface being provided with a backing layer, the skin-facing surface being interrupted by a pattern of cavities, and wherein the absorbent adhesive layer comprises a pharmaceutically active agent selected from analgesics and local anesthetics.

DETAILED DISCLOSURE

Figure 1:
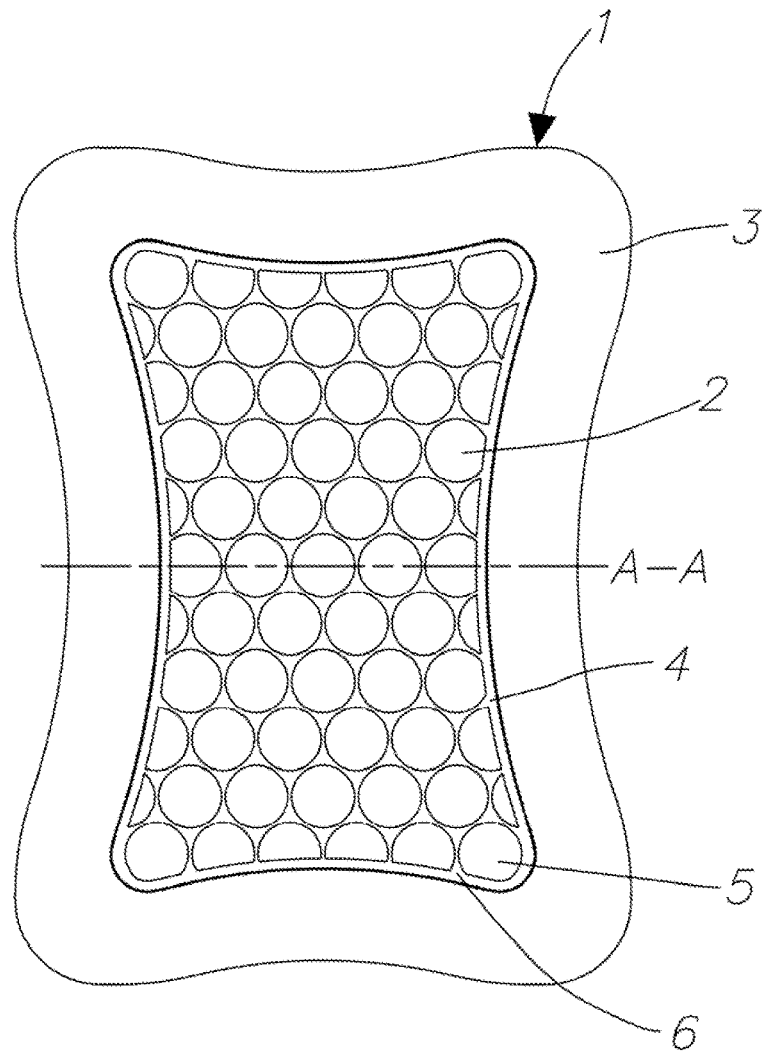
FIG. 1 shows a preferred embodiment of the invention seen in perspective: a medical dressing (1) comprising a central portion (2) surrounded by a border portion (3). The central portion comprises a network of interconnected cavities (4) between dots (5) of absorbent adhesive comprising pharmaceutically active agent(s). Along the transition zone between the central portion (2) and the border portion (3) is a channel (6), connected to the cavities (4).
Figure 2:
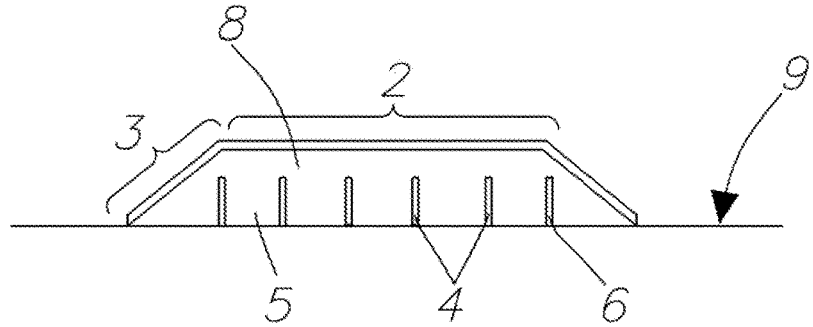
FIG. 2 shows a cross-section of the dressing along the A-A line in FIG. 1, disclosing a backing layer (7), facing away from the skin surface (9) and coated on the skin facing surface with an absorbent adhesive layer comprising pharmaceutically active agent(s) (8). In the skin facing surface are embossed cavities (4) with discrete absorbent adhesive zones (5).

The medical dressing of the present invention comprises an absorbent adhesive layer having a skin-facing surface and a non-skin-facing surface, the non-skin-facing surface being provided with a backing layer, the skin-facing surface of the absorbent adhesive layer being interrupted by a pattern of cavities, and wherein the absorbent adhesive layer comprises a pharmaceutically active agent.

The medical dressing of the invention facilitates increased liquid handling capacity by firstly providing a reservoir in the pattern of cavities for liquid to be stored in the dressing until it can be absorbed. In this manner the skin-facing absorbent adhesive surrounding the cavities may be kept relatively free of liquid and adhere to the skin while the absorption is initiated. The initial absorbent capacity of absorbent adhesives is a function of the surface area and thus a faster absorption is achieved when a larger surface gets in contact with the liquid. Accordingly, the cavities secondly provide for a faster absorption due to an increased surface area.

Prior solutions of wound dressing are typically focused on leading the liquid away from the wound in vertical direction, towards the backing layer, the thicker the dressing the more capacity for leading away any liquid. A release of a pharmaceutically active agent may at least partly be dependent on migration through the layer wherein it is contained, hence the thicker the layer the slower the release. The present inventors have by the present medical dressing found a solution to this problem which functions independent of any release aids like e.g. chemical enhancers.

The present inventors have surprisingly found that despite the liquid becoming absorbed more quickly—going from the wound surface into the dressing—an active agent in the absorbent layer at the same time is released faster initially compared to a dressing without such a pattern of cavities. It has been found that by having a pattern of cavities in the absorbent adhesive layer the release is increased within the first 30 minutes of application. This gives an advantage when a fast onset of therapeutic effect of the active agent is desirable, such as e.g. when a blister causes a subject pain and a fast pain relief is desirable.

In one embodiment of the invention, the amount of pharmaceutically active agent that is released after 30 minutes is at least 20% increased compared to the amount released from such a medical dressing without said pattern of cavities. Due to the increased initial release an improved short term effect can be obtained without increasing the concentration of active agent in the medical dressing. The release study of Example 3 herein exemplifies how a pattern of cavities increases the released amount of active agent as compared to an identical dressing without said pattern of cavities. In a preferred embodiment of the invention, the amount released is at least 25% increased, and more preferably at least 30% increased compared to the amount released from such a medical dressing without said pattern of cavities. In Example 3 is provided a method of how the amount of active agent released after 30 minutes may be determined in a comparative study, and there is given a calculation example.

Medical dressings according to the invention comprise a pharmaceutically active agent, and may comprise one or more further pharmaceutically active agents. When there are more than one agent these may be within the same or different therapeutic group, such as e.g. pain relief and antibacterial. The term "pharmaceutically active agent" is to be understood broadly and includes any agent that may be delivered from the medical dressing providing a physiological or pharmacological effect in a human this includes both therapeutic and prophylactic effects. The term furthermore includes agents that produce localized and/or systemic effects. In a preferred embodiment of the invention, the pharmaceutically active agent is an agent producing a localized effect. The term pharmaceutically active agent furthermore includes various forms of the active component of such an agent, for example, but not limited to, molecular complexes, crystalline forms, amorphous forms, solvates, such as hydrates, or pharmaceutically acceptable salts of any salt forming agent.

Pharmaceutically active agent suitable for the present invention may for example be an analgesics including nonsteroidal anti-inflammatory drugs (NSAIDs), anesthetics, local anesthetics, antimicrobial agents including antibacterial agents and anti-fungal agents, anti-viral agents, or hormonal agents, or combination of these if two or more pharmaceutically active agents are incorporated. In a preferred embodiment of the invention, the pharmaceutically active agent is selected from analgesics, local anesthetics, antimicrobial agents, and anti-viral agents. In a more preferred embodiment of the invention, the pharmaceutically active agent is selected from analgesics and local anesthetics. In the above embodiments, a further pharmaceutically active agent may be present and it may in this case be selected from the same or a different type of therapeutic group, such as those mentioned herein above. In this manner a combination therapy providing for example pain relief and treatment or prevention of an infection in a blister may be obtained.

Analgesics may traditionally be divided into non-opiod analgesics, such as e.g. paracetamol and nonsteroidal anti-inflammatory drugs (NSAIDs); weak opioid analgesics, such as e.g. codein, dextropropoxyphene or dihydrocodeine; and strong opiod analgesics, such as e.g. morphine, buprenorphine, oxycodone, diamorphine, methadone, fentanyl, pentazocine or pethidine. In a preferred embodiment of the invention, the analgesics are topically active analgesics. These may preferably be selected from NSAIDs and topically active opioids, such as e.g. morphine, hydromorphone, oxycodone, methadone, or fentanyl; more preferably selected from NSAIDs.

NSAIDs provides an analgesic and an anti-inflammatory effect by inhibiting cyclo-oxygenase-1 and -2(COX-1 and COX-2) or by selectively inhibiting COX-2 and preventing formation of prostaglandins, the latter playing a role in the production of pain. Acetylsalicylic acid is known to only inhibit COX-1. Selective COX-2 inhibitors may be preferred to reduce the well-known adverse gastrointestinal effects arising inhibition of COX-1 when systemically administered, but are on the other hand connected with an increased risk of cardiovascular events. However, the medical dressing of the present invention allows for local administration of NSAIDs in low dosages with a fast onset of action hereby avoiding the systemic effect observed by traditional oral administration in systemically effective amounts. Examples of NSAIDs which suitably may be used in the present invention are: ibuprofen, naproxen, fenoprofen, ketoprofen, flurbiprofen, oxaprozin, loxoprofen, indomethacin, tolmetin, sulindac, etodolac, ketorolac, diclofenac, piroxicam, meloxicam, tenoxicam, droxicam, lornoxicam, isoxicam, mefanamic acid, meclofenamic acid, flufenamic acid, tolfenamic acid, celecoxib, rofecoxib, valdecoxib, celecoxib, rofecoxib, or lumiracoxib. In a preferred embodiment of the invention, the pharmaceutically active agent is selected from NSAIDs which inhibits COX-1 and COX-2, and/or those selectively inhibiting COX-2.

In one embodiment of the invention, a NSAID is selected from ibuprofen, naproxen, fenoprofen, ketoprofen, flurbiprofen, oxaprozin, loxoprofen, indomethacin, tolmetin, sulindac, etodolac, ketorolac, diclofenac, piroxicam, meloxicam, tenoxicam, droxicam, lornoxicam, isoxicam, mefanamic acid, meclofenamic acid, flufenamic acid, and tolfenamic acid. In a preferred embodiment of the invention, a NSAID is selected from ibuprofen, naproxen, fenoprofen, ketoprofen, flurbiprofen, oxaprozin, loxoprofen, indomethacin, tolmetin, sulindac, etodolac, ketorolac, diclofenac, piroxicam, meloxicam, tenoxicam, droxicam, lornoxicam, and isoxicam. In a more preferred embodiment of the invention, a NSAID is selected from ibuprofen, naproxen, fenoprofen, ketoprofen, flurbiprofen, oxaprozin, loxoprofen, indomethacin, tolmetin, sulindac, etodolac, ketorolac, and diclofenac. In another preferred embodiment of the invention, a NSAID is selected from ibuprofen, naproxen, fenoprofen, ketoprofen, flurbiprofen, oxaprozin, and loxoprofen. In a specific embodiment of the invention, a NSAID is selected from ibuprofen, diclofenac, and piroxicam. In a most preferred embodiment of the invention, the pharmaceutically active agent is ibuprofen.

Local anesthetics act by blocking the sensory nerve endings in the skin or mucous membranes. Examples of local anesthetics which may be used in the present invention and are known for their topical and surface use are: amethocaine, amylocaine, benzocaine, butacaine, butoxycaine, butyl aminobenzoate, cinchocaine, clibucaine, clormecaine, cocaine, cyclomethycaine, dimethisoquin, diperodon, dyclocaine, hexylcaine, isobutamben, ketocaine, lignocaine, myrtecaine, octacaine, oxethazaine, oxybuprocaine, parethoxycaine, pramoxine, prilocaine, propanocaine, or propipocaine, or combinations of these like e.g. prilocaine in combination with lignocaine.

Antimicrobial agents may traditionally be divided into antibacterial agents and anti-fungal agents. Examples of antibacterial agents which may be used in the present invention and which are known for their topical use are fucidic acid, sodium fucidate, retapamulin, mupirocin, oxytetracycline, polymyxin B, kanamycin, bacitracin, bacitracin zinc, or neomycin. Examples of anti-fungal agents which may be used in the present invention and which are known for their topical use are amorolfine, clotrimazole, miconazole, ketoconazole, ciclopirox, or terbinafine. Antimicrobial agents may be used in a medical dressing of the invention as the only pharmaceutically active agent, or they may be used as a further pharmaceutically active agent in addition to analgesics or local anesthetics.

Antiviral agents which suitably may be used in the present invention include agent for treatment of herpes simplex, these may preferably be aciclovir and penciclovir. Antiviral agents may be used in a medical dressing of the invention as the only pharmaceutically active agent, or they may be used as a further pharmaceutically active agent in addition to analgesics or local anesthetics.

The pharmaceutically active ingredient may be distributed homogeneously in the adhesive layer.

In a preferred embodiment of the invention, the pharmaceutically active agent is Ibuprofen in a concentration of between 0.2% to 10% w/w in the absorbent adhesive layer; more preferably in a concentration of between 0.5% to 8% w/w; even more preferably of between 0.5% to 7% w/w. Typically, the concentration may be approximately 5% w/w.

Another way of expressing the concentration of a pharmaceutically active agent is in $mg/cm^2$ of the dressing surface. In this case the thickness of the medical dressing may influence which concentration is desirable; for example if a typical dressing having a thickness of 1 mm suitably have a concentration of y $mg/cm^2$, then a similar dressing having a thickness of 2 mm suitably may have a concentration in $mg/cm^2$ of twice that (y×2 $mg/cm^2$). It is to be noted that the dressing surface here is the skin-facing surface of the dressing, irrespective of any additional surface area added within the dressing by the pattern of cavities. For example a 10×10 cm dressing with a pattern of cavities has for this purpose a surface of 100 $cm^2$. A calculation example for the relationship between % w/w and $mg/cm^2$: an absorbent adhesive layer having 4.8% w/w of active agent, and a density of 1.2 $g/cm^3$ contains 40 $mg/cm^3$ of active agent; for a layer of 1 mm this corresponds to 4 $mg/cm^2$. As is the case for the present invention the pattern of cavities will influence this number, hence the 40 $mg/cm^3$ is to be adjusted for the pattern of cavities, e.g. 33% of the surface area with a depth of 25% of the thickness of the dressing: 33%×0.25=8.25% of the volume is removed, giving 38 $mg/cm^3$, corresponding to 3.8 $mg/cm^2$.

In a preferred embodiment of the invention, the pharmaceutically active agent is Ibuprofen, wherein the amount in the absorbent adhesive layer is in a range of 0.3 $mg/cm^2$ to 10 $mg/cm^2$; preferably in a range of 0.8 $mg/cm^2$ to 10 $mg/cm^2$; more preferably in a range of 0.8 $mg/cm^2$ to 8 $mg/cm^2$. Typically, the amount may be in range of 3 to 6 $mg/cm^2$. The latter is for example preferred in embodiments of the invention, where the medical dressing—or more specifically the absorbent adhesive layer of the dressing—has a thickness of about 1 mm.

In a preferred embodiment of the invention, the pattern of cavities is a network of interconnected cavities. This may be an interconnected geometric pattern or alternatively an interconnected random pattern. In these embodiments of the invention, the liquid is distributed horizontally into the pattern of cavities, facilitating an increased and faster absorption due to exposure to a larger surface of the absorbent adhesive. Hereby, the liquid handling capacity is even further increased.

When the pattern of cavities is a network of interconnected cavities this provides a liquid distribution effect, allowing liquid in one area to spread to another area of the dressing. The spreading of liquid in the pattern of cavities may be carried out by mere flow of liquid, a capillary effect or by applying external pressure such as the user rubbing a finger over the dressing during application, or a combination thereof. Hereby, the exudates are distributed over a larger surface area of the adhesive and the zone of contact between the exudates and the adhesive is increased.

Theoretically, the spreading of exudates may enhance the risk of maceration of the underlying skin, but surprisingly it has been shown that the enhanced absorption together with the non-skin contacting areas of the cavities minimizes the risk of maceration. Accordingly, exudates may be absorbed before maceration of the surrounding skin occurs. Additionally, this combination of effects will provide moist wound healing conditions.

The medical dressing of the invention is especially suited for wounds, skin abrasions and blisters. After rupturing a blister it may for instance continue to produce liquid especially when under continued pressure. The exudates to be absorbed by the dressing may be any liquid from a wound or the skin, such as blood, wound exudates, or liquid from a ruptured blister.

By the term "absorbent adhesive layer" is meant that the adhesive layer comprises an absorbent component. An absorbent component may be one or more of hydrocolloid particles, super absorbent particles, or fibers. The presence of hydrocolloid in the adhesive layer provides a good environment for moist wound healing as well as for other skin conditions. By incorporating an amount of hydrocolloid particles in the adhesive layer, the wound dressing is able to handle moisture in most conditions. In a preferred embodiment of the invention, the absorbent adhesive layer comprises hydrocolloids.

Suitable hydrocolloids for the dressing of the present invention include synthetic polymers prepared from single or multiple monomers, naturally occurring hydrophilic polymers or chemically modified naturally occurring hydrophilic polymers. The hydrocolloid polymers may be linear or cross-linked. Natural or chemically modified natural polymers include, but are not limited to, cellulosics, such as carboxymethyl cellulose (CMC), chitosan, pectin, guar gum, starches, dextrines, collagenes or gelatine. Synthetic polymers include, but are not limited to, polyacrylic acid, polyvinylealcohol/acetate, polyhydroxyalkyl acrylates and methacrylates, polyacrylamides, polystyrene sulfonates, polyvinyl pyrilidone, polyglycols, or copolymers, grafts or mixtures of these.

In one embodiment of the invention, the absorbent adhesive layer comprises hydrocolloid particles selected from cellulosics, chitosan, pectin, guar gum, starches, dextrines, collagens, gelatin, polyacrylic acid, polyvinylealcohol/acetate, polyhydroxyalkyl acrylates or methacrylates, polyacrylamides, polystyrene sulfonates, polyvinyl pyrilidone, polyglycols, and copolymers, grafts or mixtures of these. In a more preferred embodiment of the invention, the absorbent adhesive layer comprises hydrocolloid particles selected from cellulosics.

The adhesive of the absorbent adhesive layer of the dressing may be any suitable skin-friendly adhesive.

The skin-friendly adhesive may be any skin-friendly adhesive known per se for production of medical articles, which are to be adhered to human skin, preferably an adhesive comprising hydrocolloids or other moisture absorbing constituents for prolonging the time of use. The adhesive may suitably be of the type disclosed in U.S. Pat. Nos. 4,231,369, 4,367,732, 4,867,748, and 5,714,225. Especially preferred are the adhesives disclosed in U.S. Pat. Nos. 4,367,732, and 5,714,225.

The dressing of the present invention may in one embodiment of the invention be in the form of a mono-phase adhesive, i.e. made from one adhesive component; or in accordance with another embodiment of the invention be in the form of a two-zone adhesive, e.g. of the general type disclosed in U.S. Pat. No. 5,714,225, i.e. a part of or all of the adhesive areas of the dressing having maximum thickness being constituted by more than one type of adhesive.

The pattern of cavities are in the form of indentations or embossments in the skin-facing adhesive surface forming a pattern of skin-contacting adhesive zones, e.g. dots, separated by the embossed cavities. The skin-contacting adhesive zones may be in the form of discrete zones, surrounded by the cavities. The adhesive zones may have geometrical configurations such as circles, triangles, polygons etc. or they may have a more random configuration. Thus, the skin-facing surface of the central portion comprises discrete adhesive skin-contacting zones separated by non-skin-contacting cavities. The skin-contacting adhesive zones provide absorption capacity for absorption of wound exudates as well as they serve as a spacer, preventing the cavities from collapsing.

By cavities is herein meant indentations or embossed areas in the adhesive layer in the form of one or more zones where the adhesive layer is thinner than the adhesive layer or where the adhesive layer is absent, thus providing a three-dimensional volume void volume. The skin-facing adhesive surface of the wound dressing is interrupted at the cavities, thus there is not direct contact between adhesive and skin/wound in these cavities. The cavities may be embossed in the skin facing adhesive surface of the wound dressing. These cavities may act as reservoir chambers for the blood or wound exudates and may, when the cavities are interconnected, distribute such across a wider area. Thus the cavities may be in the form of reservoirs or interconnected channels.

In one embodiment of the invention, the medical dressing is divided into a central portion and a border portion surrounding the central portion, wherein the adhesive layer of the border portion is continuous and the absorbent adhesive layer of the central portion is interrupted by the pattern of cavities.

The adhesive layer of a border portion may be any suitable skin-friendly adhesive. The adhesive may be non-absorbent or it may comprise an absorbent component. In one embodiment, the adhesive layer of a border portion consist of the same adhesive as the adhesive of the central portion, i.e. the adhesive of the central portion and the adhesive of the border portion being an integral unit. Any absorbent component or adhesive of a border portion may independently be any of those described herein above in relation to the absorbent adhesive layer.

In embodiments of the invention where a border portion and a central portion consist of the same absorbent adhesive the pharmaceutically active agent may suitably be present in both the border portion and the central portion. In embodiments of the invention where the adhesive of a border portion and the absorbent adhesive of a central portion are different, the border portion may optionally comprise the pharmaceutically active agent.

The dressing of the present invention may consist of a backing layer and a layer of absorbent adhesive comprising a pharmaceutically active agent. Such dressing solely consists of backing layer and absorbent adhesive layer, any non-adhesive absorbent layer such as a foam pad, gauze or the like is absent. Absorbent properties of the dressing relates to the presence of an absorbent adhesive in the dressing. The adhesive layer may comprise one adhesive or it may be in the form of two or more adhesives. For example, in case that the dressing comprises a border portion and a central portion, there may be one adhesive for the border portion and another adhesive for the central portion.

When the dressing of the invention is applied to for example a bleeding wound, the droplet of blood being on top of the wound will be distributed into the cavities. The wound contacting surface of the dressing, being the adhesive parts being located in between the cavities, will contact and adhere to the skin around the cavities while the absorption is initiated. When a dressing of the invention furthermore comprises a border portion this part will have full contact and adhere to the skin and furthermore ensure that in case of very large amounts of exudates continued pressure on the dressing will not lead to leakage of liquids beyond the borders.

Thus, the cavities may be able to store excessive liquid until the adhesive is capable of absorbing it, without the excessive liquid compromising the attachment of the wound dressing by wetting the entire adhesive surface contacting the skin.

In embodiments of the invention having a border portion and a central portion, the central portion is surrounded by a border portion without cavities, thus it is a continuous skin-contacting layer. A continuous border portion, being without cavities or other interruptions, may serve as a sealing line preventing leakage from the central portion and thus serve as a stop layer as well as it ensures good adhesive tack to the skin. Such continuous layers provide no channels for liquid to escape from the central portion of the wound dressing. A border portion may constitute 10-50%, such as e.g. 15-45%, 17-40% or 20-40% of the area of the dressing. The border portion may have a width of 2.5-25 mm; more preferably 3-20 mm.

Any continuous border portion may be bevelled by having the outer periphery of the dressing having a decreased thickness. The bevelled portion may provide a smoother transition between the dressing and the skin and reduce the risk of "rolling-up" the edge of the dressing thereby reducing the wear-time. The outer periphery of the dressing may preferably be bevelled in analogy with the disclosure of U.S. Pat. No. 4,867,748 or U.S. Pat. No. 5,133,821. The edge is preferably bevelled so that the thickness adjacent to the edge does not exceed about 30% of the maximum thickness of the dressing; more preferred not exceeding 25% of the maximum thickness.

The backing layer may be any layer or film being water impervious but vapor permeable. The backing layer may be of any suitable material known per se for use in the preparation of wound dressings e.g. a foam, a non-woven layer or a polyurethane, polyethylene, polyester or polyamide film.

An especially suitable material for use as a backing layer is a polyurethane film. A preferred low friction film material is disclosed in U.S. Pat. No. 5,643,187.

The thickness of the absorbent adhesive layer may preferably be at least 0.5 mm, more preferred 0.5-2 mm and even more preferred 0.6-1.6 mm. The thickness of the adhesive layer is measured at the point where the adhesive layer is thickest and without cavities, thus the thickness is the distance from the skin contacting surface to the backing layer, measured perpendicular to the backing layer. The adhesive layer may preferably have the same thickness over the entire central portion, apart from the indentations/cavities.

In embodiments of the invention having a border portion and a central portion, the thickness of the adhesive of the border portion may be the same as the thickness of the centre portion or it may be thinner. The interface between the central portion and the border portion may be bevelled in order to facilitate a smooth transition. In one embodiment, the thickness of the border portion is 0.05 mm-0.4 mm, more preferred 0.05-0.2 mm, even more preferred 0.05-0.1 mm.

The transition line between any central portion and border portion may be in the form of an embossed channel being interconnected to the cavities. The channel may serve as an extra protection against leakage. The channel may encircle the central portion.

In one embodiment, the skin-facing surface area of the cavities constitutes at least 20% of the area of the skin-facing surface area of the absorbent adhesive layer. In one embodiment the cavities constitutes at least 25%, such as e.g. at least 30%, of the skin-facing surface of the central portion.

The cavities may be defined as three-dimensional structures defined by the skin as bottom wall, the backing layer or any absorbent adhesive layer as top wall, and edge portions of the adhesive as side walls. Each occurrence of a cavity, either as alone standing hollow or as a channel, may be defined by its width and depth. The cavities may have a width of 0.1-4 mm, such as e.g. 0.1-3 mm, 0.1-2 mm, 0.2-1.2 mm, or 0.2-0.8 mm; preferably a width of 0.2-2 mm; more preferably 0.2-1.5 mm; even more preferably 0.3-1.2 mm; and most preferably 0.3-1 mm. The width is measured at the most narrow point between the edge portions of the adhesive side walls.

The depth of the cavities, measured from the skin-facing surface to the bottom of the cavity, may be substantially the same as the thickness of the adhesive layer, leaving the backing layer above the cavity without adhesive or with only a thin layer of adhesive. In one embodiment, the depth of the cavities is less than the thickness of the absorbent adhesive layer. Thus, in this embodiment at least a thin layer of absorbent adhesive is on the backing layer at the top of the cavities. The depth of the cavities may be at least 15% of the thickness of the absorbent adhesive layer, such as e.g. at least 20%, at least 30%, at least 40%, at least 50%, or at least 75%. In one embodiment of the invention, the depth of the cavities is in a range of between 15% to 75% of the thickness of the absorbent adhesive layer; preferably between 20% to 75%, such as e.g. 20% to 50%. In a specific embodiment the depth of the cavities is 0.3-0.5 mm.

A preferred embodiment of the invention relates to a medical dressing, wherein the pattern of cavities constitutes at least 20% of the area of the skin-facing surface, and each cavity occurrence has a depth of at least 15% of the thickness of the absorbent adhesive layer and a width of 0.1-4 mm.

Another preferred embodiment of the invention relates to a medical dressing, wherein the pattern of cavities constitutes at least 25% of the area of the skin-facing surface, and each cavity occurrence has a depth of at least 20% of the thickness of the absorbent adhesive layer and a width of 0.2-2 mm, more preferably a width of 0.3-1 mm.

Yet another preferred embodiment of the present invention relates to a medical dressing comprising an absorbent adhesive layer having a skin facing surface and a non-skin-facing surface, the non-skin facing surface being provided with a backing layer, the skin-facing surface comprises a central portion and a continuous border portion surrounding the central portion, the skin-facing surface of the central portion is interrupted by a network of interconnected cavities, wherein the cavities constitutes at least 25% of the area of the skin-facing surface, and each cavity occurrence has a depth of at least 20% of the thickness of the absorbent adhesive layer and a width of 0.3-1 mm, and the absorbent adhesive layer comprises ibuprofen as pharmaceutically active agent in a concentration of between 0.2% to 10% w/w.

Apart from handling exudates, the cavities may provide shock absorbent properties, providing pressure relief due to an "air-bag" effect from the air-filled cavities.

Furthermore, whereas a traditional continuous hydrocolloid adhesive dressing may enhance the thickness in the areas where moisture is absorbed, due to vertical absorption by the hydrocolloids, the dressing of the invention may show less increase in thickness as the hydrocolloid adhesive may be able to expand horizontally.

The second aspect the invention relates to a method of treating pain in a wound, a skin abrasion or on a blister, the method comprises the step of applying to said wound, skin abrasion or blister a medical dressing comprising an absorbent adhesive layer having a skin-facing surface and a non-skin-facing surface, the non-skin-facing surface being provided with a backing layer, the skin-facing surface being interrupted by a pattern of cavities, and wherein the absorbent adhesive layer comprises a pharmaceutically active agent selected from analgesics and local anesthetics.

Any details herein described in relation to the medical dressing of the invention apply to the method of the second aspect of the invention mutatis mutandis.

EXPERIMENTAL

Example 1

Sample A: a dressing in the form of a polyurethane backing layer coated with a continuous layer of hydrocolloid adhesive, the hydrocolloid being carboxymethyl cellulose, representing state-of-the-art. The dressing was 9.6×9.6 cm and had a thickness of 1.0 mm.

Sample B: a dressing according to the invention, except that pharmaceutical active agent(s) is left out for simplicity: having a polyurethane backing layer coated with a layer of hydrocolloid adhesive, the hydrocolloid being carboxymethyl cellulose, the dressing comprises a central portion, and a border portion surrounding the central portion, the skin facing surface of edge portion of the adhesive layer is continuous and the skin facing surface of central portion is interrupted by interconnected cavities as shown in FIG. 1. The dressing was 9.6×9.6 cm and had a thickness of 1.0 mm and the cavities were 0.25 mm deep and 0.5 mm wide. The cavities comprise 33% of the skin-facing surface area of the central portion. The border portion had a width of 10 mm.

Sample C: a dressing according to the invention identical to Sample B except that part of the hydrocolloid is replaced by 1% (w/w) Ibuprofen in absorbent adhesive, corresponding to 0.8 mg/cm$^2$.

Sample D: a dressing according to the invention identical to Sample B except that part of the hydrocolloid is replaced by 5% (w/w) Ibuprofen in absorbent adhesive, corresponding to 3.8 mg/cm$^2$.

Sample E: a dressing identical to Sample A except that part of the hydrocolloid is replaced by 1% (w/w) Ibuprofen in absorbent adhesive, corresponding to 0.8 mg/cm$^2$.

Sample F: a dressing identical to Sample A except that part of the hydrocolloid is replaced by 5% (w/w) Ibuprofen in absorbent adhesive, corresponding to 4.2 mg/cm$^2$.

Example 2

Exudates Handling

A test was performed in order to show the exudates handling properties of the dressing of the invention compared to a state-of-the-art dressing with a continuous adhesive skin-contacting surface.

The samples A and B were applied to a siliconized glass plate, imitating the skin surface, and 0.9 ml artificial wound exudates (colored water) were injected through a hole in the glass plate under the dressing, to simulate a bleeding or exuding wound. Then a roller was passed over the samples to exert pressure to the dressing.

Results:

Sample A: The injected exudates formed a bubble of liquid under the central portion of the dressing, and when pressure was applied to the dressing by the roller, the liquid splashed over the skin-contacting surface of the dressing and escaped under the border portion of the dressing.

Sample B: The injected exudates were distributed in the cavities around the injection point of the dressing and when pressure was applied, the liquid was further spread out into the cavities of the dressing. No liquid escaped under the border of the dressing, the entire amount of exudates was trapped in the cavities.

Example 3

Release Rate

Purpose: Investigation of short term release rates of ibuprofen from a 1.0 mm absorbent adhesive layer, and the effect of imprinting a pattern of cavities. The release experiment mimics the use of the dressing on a highly exudating wound or blister.

Figure 3:
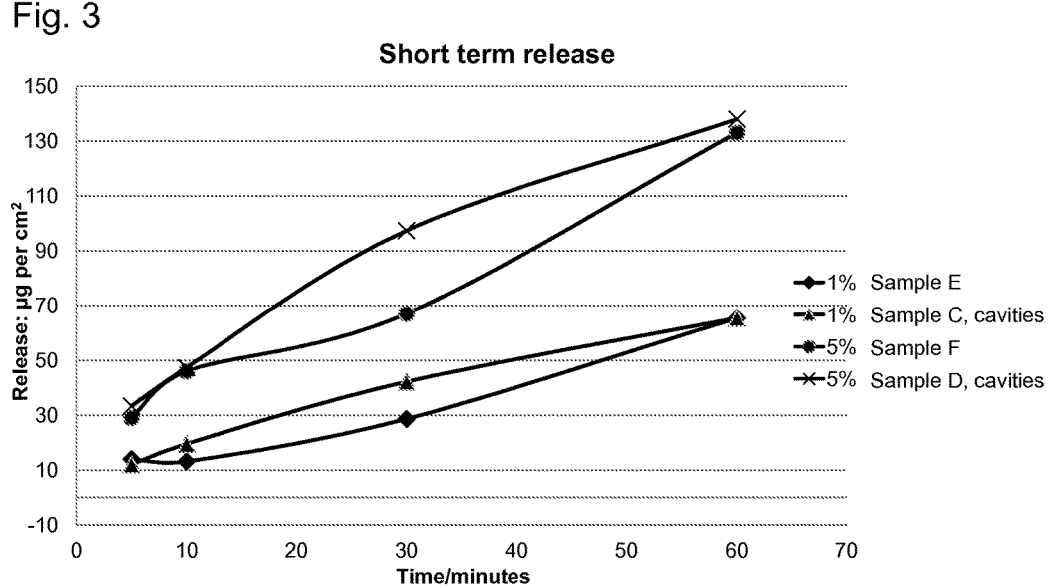
FIG. 3 shows the release of Ibuprofen in $\mu g/cm^2$ over time for four different absorbent adhesive dressings. Samples C (triangles) and D (x) according to the invention have a pattern of cavities in the skin-facing surface and a concentration of 1% (w/w) and 5% (w/w) Ibuprofen, respectively. Samples E (squares) and F (dots) are analogues absorbent adhesive dressings with continuous skin-facing surfaces and a concentration of 1% (w/w) and 5% (w/w) Ibuprofen, respectively.

Method: 2 mL Buffer (pH 6.6 10 mM Phosphate-Buffered Saline 32° C.) was added to photometry cuvettes (Polystyrene) with a 1 cm$^2$ opening, and a sample with the skin-facing surface of the absorbent adhesive layer facing the cuvette is fixed on top of each. Duplicate determinations were made. The cuvettes with the samples were then turned over (t=0) and placed in a temperature controlled oven at 32° C. At each time point (5, 10, 30, 60 minutes) two samples for each material were taken out, shaken and turned back over. The adhesive was then removed and the buffer taken out of the cuvette for HPLC quantification of the amount released from the 1 cm$^2$ affected by the buffer. Concentration/Time dependency is given in Table 1 below and in FIG. 3.

TABLE 1

| | Short term release | | | |
|---|---|---|---|---|
| | Cavities in absorbent adhesive | | No cavities - for comparison | |
| Time (min) | Sample C 1% Ibuprofen | Sample D 5% Ibuprofen | Sample E 1% Ibuprofen | Sample F 5% Ibuprofen |
| 5 | 12 µg/cm$^2$ | 33.3 µg/cm$^2$ | 14 µg/cm$^2$ | 23.8 µg/cm$^2$ |
| 10 | 19.5 µg/cm$^2$ | 47.3 µg/cm$^2$ | 13.1 µg/cm$^2$ | 37.7 µg/cm$^2$ |
| 30 | 42.2 µg/cm$^2$ | 97.4 µg/cm$^2$ | 28.6 µg/cm$^2$ | 67.7 µg/cm$^2$ |
| 60 | 65.5 µg/cm$^2$ | 138 µg/cm$^2$ | 65.4 µg/cm$^2$ | 114 µg/cm$^2$ |

Note:
1 cm$^2$ is covered by the cuvette, hence the released amount in µg is per cm$^2$.

Results and discussion: Samples C, D, E and F were tested in the above method. The release follows roughly similar curves for all four materials. Samples C and D with a pattern of cavities have a 44-48% better release within the first 30 minutes (see FIG. 3), compared to the counterpart without cavities. Thereafter, the difference is gradually cancelled out to approximately an equal release at 60 minutes.

It is furthermore observed that the method is not suitable for long term study of release as the amount of buffer and its continued proximity to the absorbent adhesive will to some extend dissolve this in a manner not observed in actual use. Hence, the long term release is in part due to a partly disintegration of the adhesive structure and not a release as such. Any data by this method after 60 minutes should therefore be used with caution.

From the data in Table 1 at 30 minutes, comparing Sample C with E and D with F, the following calculations on the released amount can be made:

$C$ vs $E$: 42.2−28.6 µg/cm$^2$=13.6 µg/cm$^2$ extra is released;

$D$ vs $F$: 97.4−67.7 µg/cm$^2$=29.7 µg/cm$^2$ extra is released;

This corresponds to an 48% and an 44% increase in the amount released, respectively, compared to the amount released from the medical dressing without a pattern of cavities.

Accordingly, the cavities provide an increased short term release allowing for a faster onset of action of the therapeutic agent as compared to medical dressing without cavities in the absorbent adhesive layer.

The invention claimed is:

1. A medical dressing comprising:
a backing layer;
an absorbent adhesive layer having a thickness measured from a skin-facing surface to a non-skin-facing surface of the absorbent adhesive layer, with the non-skin-facing surface deposited onto the backing layer and the skin-facing surface including a pattern of cavities formed in the skin-facing surface in a direction toward the backing layer, with each cavity in the pattern of cavities having a cavity depth in a range from 15% to 75% of the thickness of the absorbent adhesive layer; and
a pharmaceutically active agent distributed at a first concentration in the absorbent adhesive layer;
wherein a comparative medical dressing has a comparative absorbent adhesive layer deposited onto a comparative backing layer with the pharmaceutically active agent distributed at the first concentration in the comparative absorbent adhesive layer, and with the comparative absorbent adhesive layer characterized by an absence of cavities formed in a surface of the comparative absorbent adhesive layer in a direction toward the comparative backing layer;

wherein the pattern of cavities adapts the medical dressing to release the pharmaceutically active agent from the absorbent adhesive layer at a higher release rate than the comparative medical dressing releases the pharmaceutically active agent from the comparative absorbent adhesive layer.

2. The medical dressing according to claim 1, wherein the pharmaceutically active agent is selected from a group consisting of analgesics, local anesthetics, antimicrobial agents, and anti-viral agents.

3. The medical dressing according to claim 1, wherein the pharmaceutically active agent is selected from a group consisting of analgesics and local anesthetics.

4. The medical dressing according to claim 1, wherein the pharmaceutically active agent is selected from a group consisting of nonsteroidal anti-inflammatory drugs (NSAIDs).

5. The medical dressing according to claim 1, wherein the pharmaceutically active agent is one of ibuprofen, naproxen, fenoprofen, ketoprofen, flurbiprofen, oxaprozin, loxoprofen, indomethacin, tolmetin, sulindac, etodolac, ketorolac, diclofenac, piroxicam, meloxicam, tenoxicam, droxicam, lornoxicam, isoxicam, mefanamic acid, meclofenamic acid, flufenamic acid, tolfenamic acid, celecoxib, rofecoxib, valdecoxib, celecoxib, rofecoxib, or lumiracoxib.

6. The medical dressing according to claim 1, wherein the pharmaceutically active agent is ibuprofen.

7. The medical dressing according to claim 1, wherein the pattern of cavities adapts the medical dressing to release the pharmaceutically active agent from the absorbent adhesive layer at the higher release rate of at least 20% greater than a release rate of the comparative medical dressing in a period of 30 minutes.

8. The medical dressing according to claim 1, wherein the higher release rate of the pharmaceutically active agent from the absorbent adhesive layer is up to 48% greater than a release rate of the pharmaceutically active agent from the comparative absorbent adhesive layer over an initial period of 30 minutes.

9. The medical dressing according to claim 1, wherein the pharmaceutically active agent is Ibuprofen in a concentration of between 0.2% to 10% w/w in the absorbent adhesive layer.

10. The medical dressing according to claim 1, wherein the pharmaceutically active agent is Ibuprofen in an amount in the absorbent adhesive layer in a range of 0.3 mg/cm$^2$ to 10 mg/cm$^2$.

11. The medical dressing according to claim 1, wherein the absorbent adhesive layer comprises hydrocolloids.

12. The medical dressing according to claim 1, wherein the pattern of cavities is a network of interconnected cavities.

13. The medical dressing according to claim 12, wherein the network of interconnected cavities provides a liquid distribution effect, allowing liquid in one area to spread to another area.

14. The medical dressing according to claim 1, wherein the pattern of cavities is in the form of an interconnected geometric pattern of cavities.

15. The medical dressing according to claim 1, wherein the pattern of cavities is in the form of an interconnected random pattern of cavities.

16. The medical dressing according to claim 1, wherein the thickness of the absorbent adhesive layer is at least 0.5 mm.

17. The medical dressing according to claim 1, wherein the skin-facing surface area of the cavities is at least 20% of the skin-facing surface area of the absorbent adhesive layer.

18. The medical dressing according to claim 1, wherein the dressing is divided into a central portion and a border portion surrounding the central portion, wherein the absorbent adhesive layer of the border portion is continuous and the absorbent adhesive layer of the central portion is interrupted by the pattern of cavities.

19. The medical dressing according to claim 1, wherein the backing layer is a polyurethane film.

\* \* \* \* \*